United States Patent [19]

Bunel et al.

[11] Patent Number: 5,986,126
[45] Date of Patent: Nov. 16, 1999

[54] PROCESS FOR THE PRODUCTION OF 6-AMINOCAPRONITRILE AND/OR HEXAMETHYLENEDIAMINE

[75] Inventors: Emilio Enrique Bunel; Theodore Augur Koch; Ronnie Ozer, all of Wilmington, Del.; Shawn Homer Phillips, Canyon Country, Calif.; Sourav Kumar Sengupta, Wilmington, Del.

[73] Assignee: E. I. du Pont de Nemours and Company, Wilmington, Del.

[21] Appl. No.: 09/236,520

[22] Filed: Jan. 25, 1999

[51] Int. Cl.[6] .................................................. C07C 255/00
[52] U.S. Cl. ........................................... 558/353; 558/452
[58] Field of Search ....................................... 558/452, 353

[56] References Cited

U.S. PATENT DOCUMENTS 5,827,938  10/1998  Schnurr et al. ........................ 558/452

Primary Examiner—Johann Richter
Assistant Examiner—Joseph Murray

[57] ABSTRACT

Process for producing 6-aminocapronitrile and/or hexamethylenediamine by hydroformylating 3-pentenenitrile, isolating a formylvaleronitrile (FVN) mixture from the hydroformylation reaction product, reductively aminating the FVN mixture and isolating the desired product.

10 Claims, No Drawings

PROCESS FOR THE PRODUCTION OF 6-AMINOCAPRONITRILE AND/OR HEXAMETHYLENEDIAMINE

BACKGROUND OF THE INVENTION

The present invention relates to a process for the production of 6-aminocapronitrile (ACN) and/or hexamethylenediamine (HMD) by a process in which 3-pentenenitrile (3-PN) is hydroformylated to produce a hydroformylation reaction product which contains a mixture of isomers of formylvaleronitrile, isolating the mixture of isomers from the hydroformylation reaction product, and then reductively aminating the mixture of FVN isomers to produce a reductive amination reaction product which contains ACN and/or HMD, either or both of which can be isolated by fractional distillation.

German Patent Application 19631521 discloses a process in which at least one of 2-, 3-, and 4-pentenenitrile is reacted with carbon monoxide and hydrogen in the presence of a catalyst containing at least one Group VIII metal to produce a mixture containing 5-FVN, 4-FVN, and 3-FVN. 5-FVN is first isolated from the mixture and then reacted with ammonia and hydrogen in the presence of a catalyst that contains at least one Group VIII metal to produce ACN and/or HMD. The application discloses the use of distillation as a preferred means of separating 5-FVN from the mixture of 5-FVN, 4-FVN, and 3-FVN.

German Patent Application 19631522 discloses a process for the preparation of ACN and/or HMD by reacting 5-FVN with ammonia and hydrogen in the presence of a catalyst selected from the group consisting of metals or metal compounds of rhenium, copper and elements of Group VIII.

The purification of 5-FVN by fractional distillation from a mixture of 3-, 4-, and 5-formylvaleronitriles can be difficult, due to the instability of the formyl, i.e. aldehyde, group and the level of vacuum necessary to separate and purify the 5-FVN. The instability of the aldehyde group can lead to a loss of FVN due to aldol condensation, and the high vacuum needed for the distillation is impracticable commercially. There is need, therefore, for a process for making HMD and/or ACN in a manner that minimizes 5-FVN loss from aldol condensation, and avoids the need for low pressure fractional distillation to separate 5-FVN from a mixture of 3-, 4-, and 5-formylvaleronitriles.

SUMMARY OF THE INVENTION

This need is met by the present invention, which is a process for making hexamethylenediamine (HMD) and/or 6-aminocapronitrile (ACN) comprising:

(A) reacting 3-pentenenitrile with hydrogen and carbon monoxide in the presence of a hydroformylation catalyst comprising a Group VIII element to produce a hydroformylation reaction product which comprises 2-, 3-, 4-, and 5-formylavaleronitrile (FVN);

(B) isolating from the hydroformylation reaction product an FVN mixture which comprises 2-, 3-, 4-, and 5-FVN;

(C) reacting the FVN mixture with ammonia and hydrogen in the presence of a reductive amination catalyst comprising at least one element selected from the group comprising elements of Groups IB, VIB, VIIB, and VIII of the Periodic Table, to obtain a reductive amination reaction product which comprises hexamethylenediamine and/or 6-aminocapronitrile; and (D) isolating by fractional distillation the hexamethylenediamine and/or 6-aminocapronitrile from the reductive amination reaction product.

DETAILED DESCRIPTION

The hydroformylation of 3-pentenenitrile (i.e., the reaction of 3-pentenenitrile with carbon monoxide and hydrogen) is carried out in the presence of a Group VIII element catalyst. The temperature can vary from room temperature to about 200° C. and preferably between 50 and 150° C. The pressure is preferably between 0.15 and 10 MPa and more preferably 0.2 to 5 MPa.

Preferred catalysts are rhodium compounds. Examples of suitable compounds include $Rh(CO)_2(DPM)$, [$DPM=t-C_4H_9-COCHCO-t-C_4H_9$]; $Rh(CO)_2(acac)$, [acac=acetylacetonate]; $Rh_2O_3$; $Rh_4(CO)_{12}$; $Rh_6(CO)_{16}$; [$Rh(OAc)_2]_2$, [OAc=acetate]; and $Rh(ethylhexanoate)_2$. Preferably, the catalyst is $Rh(CO)_2(acac)$, $Rh(CO)_2(DPM)$, or $[Rh(OAc)_2]_2$.

These catalysts may be used in combination with ligands such as phosphine, phosphonites, phosphinites, or phosphite compounds. Examples of such ligands include, triarylphosphites such as triphenylphosphite; triarylphosphines, such as triphenylphosphine; and bis(diarylphosphino)alkanes, such as diphenylphosphinoethane. In addition, polydentate phosphite compounds may be used as ligands. An example of these includes:

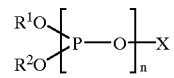

where $R^1$ and $R^2$ are the same or different mono-valent aryl groups, X is an n-valent organic bridging group, and n is an integer between 2 and 6. $R^1$ and $R^2$ may be substituted. Such ligands are described, for example, in U.S. Pat. No. 5,710,344, the disclosure of which is incorporated herein by reference.

The mole ratio of 3-penetenenitrile to catalyst is generally 100:1 to 100,000:1, preferably 500:1 to 10,000:1. The ratio of ligand to rhodium is typically between 0.5:1 and 10:1.

The ratio of hydrogen to carbon monoxide for the hydroformylation reaction is typically in the range of 100:1 to 1:10, preferably in the range of 4.0:1 to 0.5:1. Inert gases may also be present in the hydrogen and carbon monoxide feed stocks.

The hydroformylation reaction may be performed in the presence of a solvent. Suitable solvents include inert solvents or a solvent consisting primarily of the hydroformylation products themselves. Suitable inert solvents include aromatic hydrocarbons, nitrites, ethers, amides and urea derivatives, saturated hydrocarbons and ketones. Some examples of suitable solvents include toluene, cyclohexane, benzene, xylene, Texanol® (2,2,4-trimethyl-1,3-pentanediol monoisobutyrate), diphenylether, tetrahydrofuran, cyclohexanone, benzonitrile, N-methylpyrrolidinone, and N,N'-dimethylethylurea.

The hydroformylation reaction can be performed in a continuous or batch mode. The reaction can be performed in a variety of reactors such as bubble column reactors, continuously stirred tank reactors, trickle bed reactors, and liquid-overflow reactors. Unreacted hydrogen, carbon monoxide, 3-pentenenitrile, and any solvent may be recovered and recycled to the hydroformylation reactor.

The hydroformylation reaction produces a reaction product which comprises 2-, 3-, 4-, and 5-formylvaleronitriles. The hydroformylation reaction product, thus obtained, contains unconverted pentenenitriles, FVN isomers, catalyst, and high boilers. The separation of the FVN mixture from the catalyst and high boilers can be effected by utilizing thermally-gentle evaporation techniques, known to those skilled in the art. Such techniques include the use of single stage flash evaporators, such as rolling-film evaporators, falling-film evaporators, or wiped-film evaporators. High boilers and catalyst separated from the FVN mixture can be recycled back to the hydroformylation reactor.

To avoid the decomposition of the catalyst and FVN mixture, a short contact time during flash evaporation is generally preferred. The contact time can vary between 1 second and 1 hour and preferably is between 1 and 5 minutes. The flash evaporation is carried out under commercially-viable operating conditions. The temperature should be in the range of 75 to 200° C. The preferred range being 100 to 130° C. The pressure can vary from 13.3 to 1333 Pa, preferably from 66.6 to 666.5 Pa.

The prior art process described in German Patent Application 19631521 involves the step of separating 5-FVN from a mixture of its isomers before reductively aminating it. This step of separating 5-FVN from its isomers is believed to lead to a loss of 5-FVN resulting from aldol condensation reaction. The Comparative Example, below, shows that 5-FVN is decomposed under conditions which are believed to be required for implementing this separation on an industrial scale.

More specifically, the aldehyde group of 5-formylvaleronitrile (5-FVN) decomposes at a temperature of 159° C. at $5.3 \times 10^{-3}$ MPa pressure, and requires a vacuum of less than about $1.3 \times 10^{-3}$ MPa in order to prevent significant aldehyde decomposition. The purification of 5-FVN by distillation cannot be performed practically on an industrial scale due to the very low pressures (less than about $1.3 \times 10^{-3}$ MPa) required during the distillation in order to prevent decomposition of the aldehyde groups of the various FVN isomers. To overcome these problems, according to the present invention, it is important that 5-FVN not be separated from its non-linear analogs (4-FVN, 3-FVN, and 2-FVN) prior to the next step in the process, reductive amination. Separation of the mixture of FVN isomers requires either a distillation with a vacuum that is too low to be commercially attractive, or at temperatures that are so high that they promote loss of 5-FVN as a result of an aldol condensation reaction.

In the next step of the present process, the mixture of formylvaleronitriles, comprising 5-FVN, 4-FVN, 3-FVN, and 2-FVN is reductively aminated. In this step, the mixture of formylvaleronitriles (FVNs) is reacted with ammonia and hydrogen in the presence of a reductive amination catalyst.

Typical product mixtures include 6-aminocapronitrile (ACN), 2-methyl-5-aminovaleronitrile (a branched ACN isomer), 3-methyl-5-aminovaleronitrile (a branched ACN isomer), hexamethylenediamine (HMD), 2-methylpentamethylene-diamine (MPMD), and 2-ethyltetramethylenediamine (ETMD).

The reductive amination catalyst contains at least one element selected from elements of Groups IB, VIB, VIIB, and VIII of the Periodic Table. Preferred catalysts are selected from the group consisting of iron, cobalt, nickel, ruthenium, rhodium, palladium, osmium, copper, chromium, iridium, and platinum. The most preferred catalyst is ruthenium metal or a ruthenium compound. The catalysts may be in the zero oxidation state or in the form of a chemical compound and may be supported, unsupported or Raney-type.

Preferred supports include titanium dioxide, porous aluminum oxide, silicon dioxide, aluminum siliciate, lanthanum oxide, zirconium dioxide, magnesium oxide, zinc oxide, zeolites and activated charcoal. Particularly preferred supports are titanium dioxide, porous aluminum oxide, silicon dioxide, zirconium dioxide, and activated charcoal. It is also possible to use a mixture of more than one support or more than one catalyst element.

The method of placing the catalyst on a support is not critical. Several methods are known in the art. One method involves applying a solution of salt or oxide to the support, drying the support, and then reducing the salt or oxide. Another method involves applying a salt that is easily thermally decomposed to form a catalytically active species. Suitable salts include carbonyl or hydride complexes of one or more of the Group IB, VIB, VIIB, and VIII elements. Catalytically active metals can be applied to a support by vapor deposition or by flame spray.

Catalytically active metal is generally applied to the support at 0.1 to 90 percent by weight of the total supported catalyst, preferably at 0.5 to 40% by weight, more preferably 2 to 10% by weight. When the product of the reductive amination is HMD, 5–15% by weight is preferred. When the product is 6-aminocapronitrile, 1 to 7.5% by weight is preferred.

The reductive amination step of the present invention may be performed in a fixed bed reactor in which the reductive amination catalyst is present. An advantage to the fixed bed reactor is that the separation of reactants and products from the catalyst is simple. The reductive amination reaction may also be carried out in a slurry reactor (batch, continuous stirred tank reactor or bubble column reactor, for example) where the catalyst is present in a slurry during the reductive amination. In this mode, the catalyst may be removed by using centrifugal action or filtration.

A wide range of suitable catalyst concentrations may be used. The amount of catalyst per reactor is generally dependent on the reactor type. For a fixed bed reactor, the volume of catalyst per reactor will be high, while in a slurry reactor, the volume will be lower. Typically, in a slurry reactor, the catalyst will make up 0.1 to about 30 weight percent of the reactor contents. Preferably, the catalyst is 1 to 15% by weight of the reactor contents.

Typically the reductive amination reaction is performed at a temperature of 40 to 150° C., preferably 75 to 125° C. Typical pressures are 2 to 35 MPa, preferably 4 to 12 MPa.

The molar ratio of hydrogen to total formylvaleronitrile mixture is typically equal to or greater than 1:1, preferably 1:1 to 100:1, more preferably 1:1 to 50:1.

The reductive amination reaction is preferably performed in a liquid ammonia solvent. Typically, a mole ratio of 1:1 to 80:1 of ammonia to total formylvaleronitrile mixture can be used, preferably 10:1 to 50:1. An additional solvent may be used. Such solvents include alcohols, esters, hydrocarbons, tetrahydrofuran (THF), dioxane, and ammonium hydroxide. Of these additional solvents, lower alcohols, such as methanol and ethanol, THF, and dioxane are preferred. The weight ratio of the additional solvent to total formylvaleronitrile mixture is typically 0.1:1 to 5:1.

After the reductive amination is complete, any unreacted hydrogen and ammonia may be removed by flash distillation and recycled for further use in the reductive amination reaction. 6-Aminocapronitrile and/or hexamethylenediamine may then be separated from the other products by fractional distillation at moderate pressures.

The product of the reductive amination is a mixture comprising ACN and its branched isomers, HMD, 2-methylpentamethylenediamine (MPMD), 2-ethyltetramethylenediamine (ETMD). The mixture may be distilled at a pressure of $1.3 \times 10^{-3}$ MPa to $6.5 \times 10^{-2}$ MPa preferably, $6.5 \times 10^{-3}$ MPa to $3.5 \times 10^{-2}$ MPa. In one configuration of the process, water, amines, and branched ACNs (2-methyl-5-aminovaleronitrile, 3-methyl-5-aminovaleronitrile) are first separated from the linear ACN by stripping, such that highly pure linear ACN is produced as the bottoms of the distillation. The resulting distillate stream, a mixture comprising HMD, MPMD, ETMD and branched ACNs, is distilled again to remove MPMD, ETMD, and water, the lowest boiling components. The resulting bottoms stream can then be refined to remove pure HMD from the higher boiling branched ACNs. Typically, the temperature is between 100 and 250° C., preferably 140 to 200° C.

An alternative refining scheme could be sequenced as follows: the mixture containing linear and branched ACNs, HMD, MPMD, ETMD, and water is distilled to remove the MPMD, ETMD, and water first. The resulting bottoms stream is distilled to remove pure HMD in the distillate. The bottoms stream from this distillation is then distilled again to separate branched ACNs (as distillate) from the linear ACN. The temperatures and pressures used in this scheme are similar to those stated above.

The invention is illustrated by the following examples, which are not intended to limit the scope of the invention.

COMPARATIVE EXAMPLE

According to German Patent Application 19631521, the distillation of a mixture of 3-, 4-, and 5-formylvaleronitrile can be performed economically on an industrial scale, at no lower than 10 mm Hg pressure (measured at the top of the distillation column). In order to maintain such a condition at the top of a packed column, the pressure and temperature at the reboiler (distillation pot) will be at least $2.0 \times 10^{-3}$ MPa and 130° C. (boiling point of 5-FVN at $2.0 \times 10^{-3}$ MPa), respectively. An experiment was performed to simulate the decomposition of 5-formylvaleronitrile at the operating condition mentioned above. Care was taken to eliminate 5-cyanovaleric acid, which is known to enhance the rate of aldol condensation reaction. Furthermore, the distillation was carried out in an anaerobic glove box in order to avoid the facile oxidation of 5-formylvaleronitrile to 5-cyanovaleric acid.

To a 100 cc 3-necked flask was added a mixture of 3-, 4-, and 5-formylvaleronitrile (50.72 gm of 99.34%. 5-FVN, and the rest being 3- and 4-FVN). The flask was fitted with a nitrogen-cooled condenser, thermometer, and a rubber septum, to withdraw samples for subsequent work-up and analysis. The top of the condenser was connected to a vacuum pump, and the pressure was measured using a Setra Datum 2000 pressure gauge. A leak-valve was installed in the vacuum line to bleed nitrogen into the system, to maintain and control the desired pressure ($2.0 \times 10^{-3}$ MPa) in the distillation flask. The flask was heated in a heating mantle, and a uniform temperature was maintained in the flask by gently stirring the content of the flask with a magnetic stir bar. Samples were withdrawn at specified time intervals and analyzed by gas chromatography (GC) after adding an internal standard, N-methylpyrrolidinone (NMP), and diluent (ethanol). The decomposition of 5-FVN as a function of time is presented in Table A. The results in Table A show that the separation of 5-FVN from a mixture containing it and its isomers results in a 12.6% loss of 5-FVN at 160 minutes after the commencement of the experiment, or 120 minutes after a steady-state condition was reached at about 40 minutes. The loss reached 31.1% at 235 minutes after the commencement of the experiment.

TABLE A

Decomposition of 5-FVN

| Time (min) | Temperature (° C.) | Pressure (mm Hg) | Ratio of 5FVN/NMP (gm/gm) | Decomp. of 5FVN (%) |
|---|---|---|---|---|
| 0 | 30 | 15.1 | 31.72 | 0.0 |
| 40 | 130 | 15.3 | 31.41 | 1.0 |
| 70 | 134 | 15.3 | 31.27 | 1.4 |
| 100 | 134 | 15.3 | 30.20 | 4.8 |
| 130 | 133 | 15.1 | 29.10 | 8.3 |
| 160 | 134 | 14.8 | 27.73 | 12.6 |
| 235 | 133 | 15.3 | 21.86 | 31.1 |

EXAMPLES

In the following examples, all parts, proportions, and percentages are by moles, unless otherwise indicated.

General Reductive Amination Procedure:

Unless otherwise specified, the reductive amination of a mixture of 3-, 4-, and 5-formylvaleronitrile is carried out in a 300 cc autoclave designed and fabricated by Autoclave Engineers. The 300 cc reactor was constructed of Hastelloy-C with a Maximum Allowable Working Pressure (MAWP) of about 35 MPa at 300° C. The mixing in the reactor was performed with a magnetically coupled impeller, mounted on a hollow shaft and driven by an electric motor. The speed of the stirrer was monitored with a stroboscopic light. The reactor was heated with a 400 Watt external band heater.

The reactor was provided with a thermocouple insert, rupture disc, and two ⅛ inch dip legs fitted with 5µ stainless steel frits for liquid addition into the reactor, and product withdrawal from the reactor, respectively.

Example 1

6-Aminocapronitrile Synthesis Using 3.5% $Ru/TiO_2$ Catalyst

15 Grams of a mixture of 3-,4-,and 5-FVN (66.5% 5-FVN), 125 gm of tetrahydrofuran, 1 g of N-methylpyrrolidinone (NMP, internal standard), and 1.5 g of 3.5% $Ru/TiO_2$ catalyst were loaded in the reactor. The autoclave was sealed, flushed with hydrogen several times and pressure tested at 3.5 MPa. After ensuring that there were no leaks, 15 g of ammonia was added to the reactor and held at room temperature for 15 minutes. The reactor was then pressurized with hydrogen up to 7 MPa at room temperature and the reactor was heated to 110° C. under autogenous pressure. The reaction was carried out for 4 hours and 2 cc samples were withdrawn at specified time intervals. The results appear in Table 1.

TABLE 1

| Time on Stream (h) | Conversion of 5-FVN (%) | Selectivity of ACN (%) | Yield of ACN (%) |
|---|---|---|---|
| 0.00 | 0.0 | 0.0 | 0.0 |
| 0.25 | 0.0 | 0.0 | 0.0 |
| 0.50 | 88.3 | 0.0 | 0.0 |
| 1.00 | 91.9 | 0.0 | 0.0 |
| 1.50 | 100.0 | 17.9 | 17.9 |
| 2.00 | 100.0 | 38.9 | 38.9 |
| 3.00 | 100.0 | 44.5 | 44.5 |
| 3.50 | 100.0 | 55.9 | 55.9 |
| 4.00 | 100.0 | 59.4 | 59.4 |

Example 2

6-Aminocapronitrile Synthesis Using 5% $Ru/TiO_2$ Catalyst

Example 1 was repeated at 110° C. with a mixture of 3-, 4-, and 5-FVN (70.2% 5-FVN) using 5% $Ru/TiO_2$ catalyst. The results are shown in Table 2.

TABLE 2

| Time on Stream (h) | Conversion of 5-FVN (%) | Selectivity of ACN (%) | Yield of ACN (%) |
|---|---|---|---|
| 0.00 | 0.0 | 0.0 | 0.0 |
| 0.25 | 23.2 | 0.0 | 0.0 |
| 0.50 | 95.0 | 8.7 | 8.2 |

TABLE 2-continued

| Time on Stream (h) | Conversion of 5-FVN (%) | Selectivity of ACN (%) | Yield of ACN (%) |
|---|---|---|---|
| 1.00 | 97.2 | 4.3 | 4.1 |
| 1.50 | 99.6 | 22.6 | 22.5 |
| 2.00 | 99.2 | 40.3 | 39.9 |
| 3.00 | 100.0 | 56.3 | 56.3 |
| 3.50 | 100.0 | 68.4 | 68.4 |
| 4.00 | 100.0 | 70.2 | 70.2 |

Example 3

6-Aminocapronitrile Synthesis Using 5% Ru/Carbon Catalyst

Example 1 was repeated at 110° C. with a mixture of 3-, 4-, and 5-FVN (94.5% 5-FVN) using 5% Ru/Carbon catalyst. The results are shown in Table 3.

TABLE 3

| Time on Stream (h) | Conversion of 5-FVN (%) | Selectivity of ACN (%) | Yield of ACN (%) |
|---|---|---|---|
| 0.00 | 0.0 | 0.0 | 0.0 |
| 0.25 | 0.0 | 0.0 | 0.0 |
| 0.50 | 91.7 | 0.0 | 0.0 |
| 1.00 | 98.6 | 5.0 | 4.9 |
| 1.50 | 99.5 | 18.7 | 18.6 |
| 2.00 | 100.0 | 27.6 | 27.6 |
| 3.00 | 100.0 | 40.8 | 40.8 |
| 3.50 | 100.0 | 48.0 | 48.0 |
| 4.00 | 100.0 | 51.9 | 51.9 |

Example 4

Separation of ACN from its Branched Isomers with a Moderate Pressure Distillation 200 Grams of branched and linear isomers of aminocapornitrile (ACN) were prepared in three successive batches by reductive amination of a mixture containing 3-, 4-, and 5-FVN at 110° C. and 7.7 MPa in the presence of a 5% Ru/TiO$_2$ catalyst. The product obtained form the reductive amination reaction was distilled in a single stage distillation apparatus to remove high-boilers and water. The resulting distillate fraction of 95 g, was mixed with 181 g of high purity (>99%) ACN. The resulting mixture, comprising 77.8 weight percent ACN and 6.7 weight percent of branched ACN isomers was fed to an 80-plate, 1 inch ID Oldershaw column. The distillation was initiated under a total reflux at 1.3×10$^{-2}$ MPa, with condenser temperature set at 50° C. The low-boilers and water left the column primarily through the condenser, though there was also a small low-boiler cut. The trap and first-cut material showed greater than 90 weight percent water with no ACN isomers. Distillate was then removed in 2 ml cuts at a 40:1 reflux ratio using a vapor splitting head. During the second 2 ml cut, the head temperature rose form 144 to 151° C. The analysis of the second cut showed 56 weight percent branched ACN isomers, 11 weight percent ACN, with the remainder being low boilers. The head temperature increased from 151 to 158° C. during the third cut. This cut was analyzed to be 53 weight percent of branched ACN isomers and 39 weight percent ACN. As the distillation progressed, additional cuts were taken, and the analysis of these cuts showed the presence of higher amounts of ACN. The final 70 ml cut at a 40:1 reflux ratio and a head temperature of 165° C. showed 96 weight percent ACN. The residue in the reboiler pot was analyzed after the run was over, and it was determined to be 81 weight percent ACN. The residue did not contain any detectable branched ACN isomers. This experiment shows that ACN can be separated from its branched isomers economically at moderate vacuum.

Example 5

VAPOR PRESSURES OF REACTION PRODUCTS

The vapor pressures of HMD, MPMD, and ETMD as a function of temperature were determined using a standard ebuliometric method (Reid, R. C.; Prausnitz, J. M.; and Polling, B. E. in "The Properties of Gases and Liquids," McGraw-Hill Book Co., N.Y., 1986) and expressed in the form of the Antoine equation:

$$\ln(P)=A+B/(C+T)$$

where P is in mm Hg and T is temperature in ° C.

TABLE 5

| Component | A | B | C |
|---|---|---|---|
| MPMD | 16.57552 | −3807.769 | 190.261 |
| ETMD | 16.57552 | −3807.769 | 190.261 |
| HMD | 16.26502 | −3629.384 | 176.176 |

The vapor pressures obtained from the Antoine equation may be used to design a fractional distillation process for the separation of HMD from its isomers.

What is claimed is:

1. A process for making hexamethylenediamine (HMD) and/or 6-aminocapronitrile (ACN) comprising:

(A) reacting 3-pentenenitrile with hydrogen and carbon monoxide in the presence of a hydroformylation catalyst comprising a Group VIII element to produce a hydroformylation reaction product which comprises 2-, 3-, 4-, and 5-formylavaleronitrile (FVN);

(B) isolating from the hydroformylation reaction product an FVN mixture which comprises 2-, 3-, 4-, and 5-FVN;

(C) reacting the FVN mixture with ammonia and hydrogen in the presence of a reductive amination catalyst comprising at least one element selected from the group comprising elements of Group IB, VIB, VIIB, and VIII of the Periodic Table, to obtain a reductive amination product which comprises hexamethylenediamine and/or 6-aminocapronitrile; and (D) isolating by fractional distillation the hexamethylenediamine and/or 6-aminocapronitrile from the reductive amination reaction product.

2. The process of claim 1 in which the hydroformylation catalyst is a rhodium compound.

3. The process of claim 2 in which the hydroformylation catalyst further comprises a ligand selected from the group consisting of phosphine, phosphonites, phosphinites, phosphites, and polydentate hosphites.

4. The process of claim 1 in which step (B) is carried out using a single stage flash evaporator.

5. The process of claim 1 in which the reductive amination catalyst is selected from the group consisting of iron, cobalt, nickel, ruthenium, rhodium, palladium, osmium, copper, chromium, iridium and platinum.

6. The process of claim 5 in which the reductive amination catalyst is ruthenium metal or a ruthenium compound.

7. The process of claim 6 in which the ruthenium metal or ruthenium compound is on a support selected from the group consisting of titanium dioxide, porous aluminum oxide, silicon dioxide, aluminum silicate, lanthanum oxide, zirconium dioxide, magnesium oxide, zinc oxide, zeolites, and activated charcoal.

8. The process of claim 1 in which step (C) is carried out in a fixed bed reactor or a slurry reactor.

9. The process of claim 1 in which step (D) is carried out at a pressure between $1.3 \times 10^{-3}$ and $6.5 \times 10^{-2}$ MPa and at a temperature between 100 and 250° C.

10. The process of claim 9 in which the pressure is between $6.5 \times 10^{-3}$ and $3.5 \times 10^{-2}$ MPa and the temperature is between 140 and 200° C.

* * * * *